(12) United States Patent
Li et al.

(10) Patent No.: US 12,156,726 B2
(45) Date of Patent: Dec. 3, 2024

(54) STORAGE, DISPLAY, AND ANALYSIS OF FACTORED MULTIDIMENSIONAL IMAGES

(71) Applicant: Cedars-Sinai Medical Center, Los Angeles, CA (US)

(72) Inventors: Debiao Li, South Pasadena, CA (US); Anthony Christodoulou, Los Angeles, CA (US); Yibin Xie, West Hollywood, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 746 days.

(21) Appl. No.: 17/275,592

(22) PCT Filed: Sep. 18, 2019

(86) PCT No.: PCT/US2019/051664
§ 371 (c)(1),
(2) Date: Mar. 11, 2021

(87) PCT Pub. No.: WO2020/061152
PCT Pub. Date: Mar. 26, 2020

(65) Prior Publication Data
US 2022/0099775 A1    Mar. 31, 2022

Related U.S. Application Data

(60) Provisional application No. 62/734,053, filed on Sep. 20, 2018.

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/0044* (2013.01); *G01R 33/5602* (2013.01);
(Continued)

(58) Field of Classification Search
None
See application file for complete search history.

(56) References Cited

U.S. PATENT DOCUMENTS 6,560,353 B1    5/2003  Haacke
7,005,854 B2    2/2006  Mitchell
(Continued)

OTHER PUBLICATIONS

Christodoulou et al. "Magnetic resonance multitasking for motion-resolved quantitative cardiovascular imaging", Nat Biomed Eng. Apr. 2018 ; 2(4): 215-226. doi:10.1038/s41551-018-0217-y (Year: 2018).*

(Continued)

*Primary Examiner* — Randolph I Chu
(74) *Attorney, Agent, or Firm* — Nixon Peabody LLP

(57) ABSTRACT

A method of analyzing a multidimensional image tensor containing a plurality of images comprises: performing imaging scans of a subject imaging data; generating the multidimensional image tensor from the imaging data; determining a spatial basis tensor containing basis images based on the multidimensional image tensor; determining a temporal basis tensor containing basis functions for a temporal dimension based on the multidimensional image tensor; determining a core tensor that relates the spatial basis tensor to the temporal basis tensor; pre-multiplying the core tensor and the temporal basis tensor to produce a modified temporal basis tensor; storing the spatial basis tensor and the modified temporal basis tensor; and generating an image by multiplying at least (i) at least a portion of the spatial basis tensor and (ii) at least a portion of the modified temporal basis tensor.

14 Claims, 6 Drawing Sheets

(51) Int. Cl.
| | |
|---|---|
| G01R 33/56 | (2006.01) |
| G01R 33/563 | (2006.01) |
| G06T 3/60 | (2006.01) |
| G06T 5/50 | (2006.01) |
| G06T 7/00 | (2017.01) |
| G06V 10/42 | (2022.01) |

(52) U.S. Cl.
CPC ... *G01R 33/5608* (2013.01); *G01R 33/56341* (2013.01); *G06T 3/60* (2013.01); *G06T 5/50* (2013.01); *G06T 7/0016* (2013.01); *A61B 2576/023* (2013.01); *G06T 2207/10092* (2013.01); *G06T 2207/30048* (2013.01); *G06T 2207/30056* (2013.01); *G06T 2207/30061* (2013.01); *G06V 10/42* (2022.01)

(56) References Cited

U.S. PATENT DOCUMENTS

| | | |
|---|---|---|
| 8,064,979 B2 | 11/2011 | Salla |
| 9,404,986 B2 | 8/2016 | White |
| 9,482,732 B2 | 11/2016 | Chesneau |
| 9,568,580 B2 | 2/2017 | Dale |
| 9,684,979 B2 | 6/2017 | Lu |
| 10,222,441 B2 | 3/2019 | Kaditz |
| 10,359,486 B2 | 7/2019 | Kaditz |
| 10,436,871 B2 | 10/2019 | Li |
| 2004/0249314 A1 | 12/2004 | Salla |
| 2004/0263169 A1 | 12/2004 | Mitchell |
| 2005/0273001 A1* | 12/2005 | Schmainda ........ A61B 5/7435 600/411 |
| 2010/0142781 A1 | 6/2010 | Walker |
| 2015/0296214 A1 | 10/2015 | Talib |
| 2016/0232175 A1 | 8/2016 | Zhou |
| 2017/0221234 A1 | 8/2017 | Chen |
| 2017/0285122 A1 | 10/2017 | Kaditz |
| 2017/0285123 A1 | 10/2017 | Kaditz |
| 2018/0032128 A1 | 2/2018 | Baranyi |
| 2018/0306882 A1 | 10/2018 | Li |
| 2023/0243907 A1* | 8/2023 | Liu .................... G01R 33/5608 324/309 |

OTHER PUBLICATIONS

Mørup et al. "Shift-invariant multilinear decomposition of neuroimaging data", NeuroImage 42 (2008) 1439-1450 (Year: 2008).*

Tucker, L., "Some mathematical notes on three-mode factor analysis," Psychometrika—vol. 31, pp. 279-311 (Sep. 1, 1966).

De Lathauwer, L. et al., "A multilinear singular value decomposition," Siam J. Matrix Anal. Appl., vol. 21, No. 4, pp. 1253-1278 (Apr. 18, 2000).

Stanisz, G. et al., "T1, T2 relaxation and magnetization transfer in tissue at 3T," Magnetic Resonance in Medicine 54:567-512 (Aug. 5, 2005).

Kellman, P. et al., "Multicontrast delayed enhancement provides improved contrast between myocardial infarction and blood pool," Journal of Magnetic Resonance Imaging 22:605-613 (Oct. 7, 2005).

Liang, Z., "Spatiotemporal Imaging with partially separable functions," Dept. of Electrical and Computer Engineering, and Beckman Institute for Advanced Science and Technology, University of Illinois at Urbana-Champaign, pp. 988-991 (Apr. 12, 2007).

Adluru, G. et al., "Acquisition and reconstruction of undersampled radial data for myocardial perfusion MRI," J. Magn Reson Imaging, 29(2): 466-473. doi: 10.1002/jmri.21585 (Jan. 22, 2009).

Blume, U. et al., "Interleaved T1 and T2 relaxation time mapping for cardiac applications," Journal of Magnetic Resonance Imaging 29:480-487 (Jan. 22, 2009).

Pedersen, H. et al., "Temporally constrained k-t BLAST reconstruction using principal component analysis," Magnetic Resonance in Medicine 62:706-716 (Jul. 7, 2009).

Kolda, T. et al., "Tensor decompositions and applications," SIAM Review, vol. 51, No. 3, pp. 455-500 (Aug. 5, 2009).

Giri, S. et al., "T2 qualification for improved detection of myocardial edema," Journal of Cardiovascular Magnetic Resonance, pp. 1-13 (Dec. 30, 2009).

Liu, J. et al., "Respiratory and cardiac self-gated free-breathing cardiac CINE imaging with multiecho 3D hybrid radial SSFP acquisition," Magn Reson Med. May 2010; 63(5): 1230-1237 (Apr. 23, 2010).

Huang, C. et al., "T2 mapping from highly undersampled data by reconstruction of principal component coefficient maps using compressed sensing," Magn Reson Med. May 2010; 67(5): 1355-1366 (Aug. 16, 2011).

DiBella, E. et al., "Myocardial perfusion acquisition without magnetization preparation or gating," Magnetic Resonance in Medicine 67:609-613 (Dec. 21, 2011).

Liu, J. et al., "Tensor completion for estimating missing values in visual data," Arizona State University, VRViS Research Center, 8 pages (Jan. 24, 2012).

Xue, H. et al., "Phase-sensitive inversion recovery for myocardial T1 mapping with motion correction and parametric fitting," Magnetic Resonance in Medicine 69:1408-1420 (Jun. 26, 2012).

Trzasko, J. et al., "A unified tensor regression framework for calibrationless dynamic, multichannel MRI reconstruction," Mayo Clinic, Rochester, MN, United States, Proc. Intl. Soc. Mag. Reson. Med. 21, 1 page (Jan. 1, 2013).

von Knobelsdorff-Brenkenhoff et al., "Myocardial T1 and T2 at 3T: reference values, influencing factors and implications," Journal of Cardiovascular Magnetic Resonance 2013, 15:53, 11 pages (Jun. 18, 2013).

Christodoulou, A. et al., "High-resolution cardiovascular MRI by integrating parallel imaging with low-rank and sparse modeling," Ieee Trans Biomed. Eng. Nov. 2013; 60(11): 3083-3092, 29 pages (Nov. 1, 2013).

Muehling, O. et al., "Regional heterogeneity of myocardial perfusion in healthy human myocardium: assessment wit magnetic resonance perfusion imaging," Journal of Cardiovascular Magnetic Resonance, vol. 6, No. 2, pp. 499-5074 (Jan. 1, 2014).

Sharif, B. et al., "Non-ECG-gated myocardial perfusion MRI using continuous magnetization-driven radial sampling," Magnetic Resonance in Medicine 72:1620-1628 (Jan. 7, 2014).

Lam, F. et al., "A subspace approach to high-resolution spectroscopic imaging," Magnetic Resonance in Medicine 71:1349-1357 (Feb. 4, 2014).

Yu, Y. et al., "Multidimensional compressed sensing MRI using tensor decomposition-based sparsifying transform," PLOS One, www.plosone.com, Jun. 2014, vol. 9, Issue 6, e98441 (Jun. 5, 2014).

Fu, M. et al., High-resolution dynamic speech imaging with joint low-rank and sparsity constraints, Magnetic Resonance in Medicine 73:1820-1832 (Jun. 9, 2014).

Pang, J. et al., "ECG and navigator-free four-dimensional whole-heart coronary MRA for simultaneous visualization of cardiac anatomy and function," Magnetic Resonance in Medicine 72:1208-1217 (Sep. 12, 2014).

Chen, D. et al., "Quantification of myocardial blood flow using non-ECG-triggered MR imaging," Magnetic Resonance in Medicine 74:765-771 (Sep. 16, 2014).

Kvernby, S. et al., "Simultaneous three-dimensional myocardial T1 and T2 mapping in one breath hold with 3D-QALAS," Journal of Cardiovascular Magnetic Resonance 2014, 16:102, 14 pages (Dec. 20, 2014).

Christodoulou, A., et al., "3D dynamic T1 mapping of the myocardium using a time-varying subspace," Proc. Intl. Soc. Mag. Reson. Med. 23, 1 page (Jan. 1, 2015).

Feng, L. et al., "XD-GRASP-Golden-angle radial MRI with reconstruction of extra motion-state dimensions using compressed sensing," Magnetic Resonance in Medicine 75:775-788 (Mar. 25, 2015).

Coolen, B. et al., "Three-dimensional quantitative T1 and T2 mapping of the carotid artery: Sequence design and in vivo feasibility," Magnetic Resonance in Medicine 75:1008-1017 (Apr. 28, 2015).

(56) References Cited

OTHER PUBLICATIONS

Akçakaya, M. et al., "Joint myocardial T1 and T2 mapping using a combination of saturation recovery and T2-preparation," Magnetic Resonance in Medicine 76:888-896 (Sep. 29, 2015).

Ma, C. et al., "High-resolution dynamic 31P-MRSI using high-order partially separable functions," Proc. Intl. Soc. Mag. Reson. Med. 24, 3 pages (Jan. 1, 2016).

Tamir, J. et al., "T2 shuffling: Sharp, multicontrast, volumetric fast spin-echo imaging," Magnetic Resonance in Medicine 77:180-195 (Jan. 20, 2016).

Hamilton, J. et al., "MR fingerprinting for rapid quantification of myocardial T1, T2 and proton spin density," Magnetic Resonance in Medicine 77:1446-1458 (Apr. 1, 2016).

He, J. et al., "Accelerated high-dimensional MR imaging with sparse sampling using low-rank tensors," IEEE Trans Med Imaging. Sep. 2016; 35(9): 2119-2129, 31 pages (Apr. 12, 2016).

Christodoulou, A. et al., "Fast dynamic electron paramagnetic resonance (EPR) oxygen imaging using low-rank tensors," Journal of Magnetic Resonance 270 (2016) 176-182 (Sep. 1, 2016).

Hou, M., "Tensor-based Regression Models and Applications"; Université Laval; Publication [online]. Oct. 2017 [retrieved Nov. 11, 2019]. Retrieved from internet: <URL: https://pdfs.semanticscholar.org/6252/52ad9a4bf89cb457175becd6e43a543efb80.pdf>; pp. 1-100.

International Search Report and Written Opinion for International Application No. PCT/US2019/51664, mailed Dec. 2, 2019 (8 pages).

Christodoulou, A. et al., "Magnetic resonance multitasking for motion-resolved quantitative cardiovascular imaging," Nature Biomedical Engineering 2 (2018) 215-226 (Apr. 2018).

Cheng, J. A. et al., "Comprehensive multi-dimensional MRI for the simultaneous assessment of cardiopulmonary anatomy and physiology," Scientific Reports 7:5330 (Jul. 13, 2017).

Extended European Search Report for European Application No. 19861988A, mailed May 10, 2022 (8 pages).

Shaw, J. L., "Free-Breathing, Non-ECG, T1 Mapping in the Heart," dated 2017 (115 pages).

\* cited by examiner ically relates to storage # STORAGE, DISPLAY, AND ANALYSIS OF FACTORED MULTIDIMENSIONAL IMAGES

CROSS REFERENCE TO RELATED APPLICATIONS

This application is a U.S. National Stage entry of International Application No. PCT/US19/51664, filed Sep. 18, 2019, which claims priority to and the benefit of U.S. Provisional Application No. 62/734,053, filed Sep. 20, 2018, each of which is hereby incorporated by reference herein in its entirety.

TECHNICAL FIELD

The present disclosure relates biomedical imaging and analysis. More specifically, the present disclosure relates to storing and analyzing multidimensional biomedical images utilizing tensor decomposition, selective multiplication, and factor processing.

BACKGROUND

Many types of biomedical imaging (such as MRI, CT, CAT, etc.) can be used to measure multiple varying parameters of a subject ("multidimensional imaging"). Multidimensional imaging generally involves a number of different factors that need to be taken into account, such as spatial factors (e.g., the location in or on the subject that is being images) as time-varying parameters (e.g., cardiac motion, respiration). A full set of images that captures all of the different factors can greatly increase storage requirements and computational analysis times. Aspects of the present disclosure address these and other difficulties.

SUMMARY

According to aspects of the present disclosure, a method of analyzing a multidimensional image tensor containing a plurality of images of a region of interest of a subject comprises performing one or more imaging scans on the region of interest of the subject to obtain imaging data; generating the multidimensional image tensor from the imaging data; determining, based on the multidimensional image tensor, a spatial basis tensor containing one or more basis images; determining, based on the multidimensional image tensor, one or more temporal basis tensors, each temporal basis tensor containing one or more basis functions for a respective one of a plurality of temporal dimensions; determining, based on the multidimensional image tensor, a core tensor that relates the spatial basis tensor to each of the one or more temporal basis tensors; pre-multiplying the core tensor and at least one of the one or more temporal basis tensors to produce a modified temporal basis tensor; storing the spatial basis tensor and the modified temporal basis tensor; generating at least one of the plurality of images by multiplying at least (i) at least a portion of the spatial basis tensor and (ii) at least a portion of the modified temporal basis tensor.

According to aspects of the present disclosure, a system for analyzing a multidimensional image tensor containing a plurality of images of a region of interest of a subject comprises a magnet operable to provide a magnetic field; a transmitter operable to transmit to a region within the magnetic field; a receiver operable to receive a magnetic resonance signal from the region with the magnetic field; and a processor operable to control the transmitter and the receiver, the processor being configured to: perform one or more imaging scans on the region of interest of the subject to obtain imaging data; generate the multidimensional image tensor from the imaging data; determine, based on the multidimensional image tensor, a spatial basis tensor containing one or more basis images; determine, based on the multidimensional image tensor, one or more temporal basis tensors, each temporal basis tensor containing one or more basis functions for a respective one of a plurality of temporal dimensions; determine, based on the multidimensional image tensor, a core tensor that relates the spatial basis tensor to each of the one or more temporal basis tensors; pre-multiply the core tensor and at least one of the one or more temporal basis tensors to produce a modified temporal basis tensor; store the spatial basis tensor and the modified temporal basis tensor; generate at least one of the plurality of images by multiplying at least (i) at least a portion of the spatial basis tensor and (ii) at least a portion of the modified temporal basis tensor.

According to aspects of the present disclosure, a non-transitory machine-readable medium having stored thereon instructions for analyzing a multidimensional image tensor containing a plurality of images of a region of interest of a subject, which when executed by at least one processor, cause the at least one processor to: perform one or more imaging scans on the region of interest of the subject to obtain imaging data; generate the multidimensional image tensor from the imaging data; determine, based on the multidimensional image tensor, a spatial basis tensor containing one or more basis images; determine, based on the multidimensional image tensor, one or more temporal basis tensors, each temporal basis tensor containing one or more basis functions for a respective one of a plurality of temporal dimensions; determine, based on the multidimensional image tensor, a core tensor that relates the spatial basis tensor to each of the one or more temporal basis tensors; pre-multiply the core tensor and at least one of the one or more temporal basis tensors to produce a modified temporal basis tensor; store the spatial basis tensor and the modified temporal basis tensor; generate at least one of the plurality of images by multiplying at least (i) at least a portion of the spatial basis tensor and (ii) at least a portion of the modified temporal basis tensor.

According to aspects of the present disclosure, a method of analyzing a multidimensional image tensor containing a plurality of images of a region of interest of a subject comprises performing one or more imaging scans on the region of interest of the subject to obtain imaging data; generating the multidimensional image tensor from the imaging data; determining, based on the multidimensional image tensor, a spatial basis tensor containing one or more basis images; determining, based on the multidimensional image tensor, one or more temporal basis tensors, each temporal basis tensor containing one or more basis functions for a respective one of a plurality of temporal dimensions; determining, based on the multidimensional image tensor, a core tensor that relates the spatial basis tensor to each of the one or more temporal basis tensors; and generating at least one of the plurality of images by multiplying at least (i) the core tensor, (ii) at least a portion of the spatial basis tensor and (iii) at least a portion of at least one of the plurality of temporal basis tensors.

According to aspects of the present disclosure, a system for analyzing a multidimensional image tensor containing a plurality of images of a region of interest of a subject comprises a magnet operable to provide a magnetic field; a transmitter operable to transmit to a region within the magnetic field; a receiver operable to receive a magnetic resonance signal from the region with the magnetic field; and a processor operable to control the transmitter and the receiver, the processor being configured to: perform one or more imaging scans on the region of interest of the subject to obtain imaging data; generating the multidimensional image tensor from the imaging data; determine, based on the multidimensional image tensor, a spatial basis tensor containing one or more basis images; determine, based on the multidimensional image tensor, one or more temporal basis tensors, each temporal basis tensor containing one or more basis functions for a respective one of a plurality of temporal dimensions; determine, based on the multidimensional image tensor, a core tensor that relates the spatial basis tensor to each of the one or more temporal basis tensors; and generate at least one of the plurality of images by multiplying at least (i) the core tensor, (ii) at least a portion of the spatial basis tensor and (iii) at least a portion of at least one of the plurality of temporal basis tensors.

According to aspects of the present disclosure, a non-transitory machine-readable medium having stored thereon instructions for analyzing a multidimensional image tensor containing a plurality of images of a region of interest of a subject, which when executed by at least one processor, cause the at least one processor to: perform one or more imaging scans on the region of interest of the subject to obtain imaging data; generating the multidimensional image tensor from the imaging data; determine, based on the multidimensional image tensor, a spatial basis tensor containing one or more basis images; determine, based on the multidimensional image tensor, one or more temporal basis tensors, each temporal basis tensor containing one or more basis functions for a respective one of a plurality of temporal dimensions; determine, based on the multidimensional image tensor, a core tensor that relates the spatial basis tensor to each of the one or more temporal basis tensors; and generate at least one of the plurality of images by multiplying at least (i) the core tensor, (ii) at least a portion of the spatial basis tensor and (iii) at least a portion of at least one of the plurality of temporal basis tensors.

According to aspects of the present disclosure, a method of analyzing a multidimensional image tensor containing a plurality of images of a region of interest of a subject comprises performing one or more imaging scans on the region of interest of the subject to obtain imaging data; determining, based on the imaging data, a spatial basis tensor containing one or more basis images; determining, based on the imaging data, one or more temporal basis tensors, each temporal basis tensor containing one or more basis functions for a respective one of a plurality of temporal dimensions; determining, based on the imaging data, a core tensor that relates the spatial basis tensor to each of the one or more temporal basis tensors; pre-multiplying the core tensor and at least one of the one or more temporal basis tensors to produce a modified temporal basis tensor; storing the spatial basis tensor and the modified temporal basis tensor; generating at least one of the plurality of images by multiplying at least (i) at least a portion of the spatial basis tensor and (ii) at least a portion of the modified temporal basis tensor.

According to aspects of the present disclosure, a system for analyzing a multidimensional image tensor containing a plurality of images of a region of interest of a subject comprises a magnet operable to provide a magnetic field; a transmitter operable to transmit to a region within the magnetic field; a receiver operable to receive a magnetic resonance signal from the region with the magnetic field; and a processor operable to control the transmitter and the receiver, the processor being configured to: perform one or more imaging scans on the region of interest of the subject to obtain imaging data; determine, based on the imaging data, a spatial basis tensor containing one or more basis images; determine, based on the imaging data, one or more temporal basis tensors, each temporal basis tensor containing one or more basis functions for a respective one of a plurality of temporal dimensions; determine, based on the imaging data, a core tensor that relates the spatial basis tensor to each of the one or more temporal basis tensors; pre-multiply the core tensor and at least one of the one or more temporal basis tensors to produce a modified temporal basis tensor; store the spatial basis tensor and the modified temporal basis tensor; generate at least one of the plurality of images by multiplying at least (i) at least a portion of the spatial basis tensor and (ii) at least a portion of the modified temporal basis tensor.

According to aspects of the present disclosure, a non-transitory machine-readable medium having stored thereon instructions for analyzing a multidimensional image tensor containing a plurality of images of a region of interest of a subject, which when executed by at least one processor, cause the at least one processor to: perform one or more imaging scans on the region of interest of the subject to obtain imaging data; determine, based on the imaging data, a spatial basis tensor containing one or more basis images; determine, based on the imaging data, one or more temporal basis tensors, each temporal basis tensor containing one or more basis functions for a respective one of a plurality of temporal dimensions; determine, based on the imaging data, a core tensor that relates the spatial basis tensor to each of the one or more temporal basis tensors; pre-multiply the core tensor and at least one of the one or more temporal basis tensors to produce a modified temporal basis tensor; store the spatial basis tensor and the modified temporal basis tensor; generate at least one of the plurality of images by multiplying at least (i) at least a portion of the spatial basis tensor and (ii) at least a portion of the modified temporal basis tensor.

According to aspects of the present disclosure, a method of analyzing a plurality of images of a region of interest of a subject comprises performing one or more imaging scans on the region of interest of the subject to obtain imaging data; determining, based on the imaging data, a spatial basis tensor containing one or more basis images; determining, based on the imaging data, one or more temporal basis tensors, each temporal basis tensor containing one or more basis functions for a respective one of a plurality of temporal dimensions; determining, based on the imaging data, a core tensor that relates the spatial basis tensor to each of the one or more temporal basis tensors; and generating at least one of the plurality of images by multiplying at least (i) the core tensor, (ii) at least a portion of the spatial basis tensor and (iii) at least a portion of at least one of the plurality of temporal basis tensors.

According to aspects of the present disclosure, a system for analyzing a multidimensional image tensor containing a plurality of images of a region of interest of a subject comprises a magnet operable to provide a magnetic field; a transmitter operable to transmit to a region within the magnetic field; a receiver operable to receive a magnetic resonance signal from the region with the magnetic field; and a processor operable to control the transmitter and the receiver, the processor being configured to: perform one or more imaging scans on the region of interest of the subject to obtain imaging data; determine, based on the imaging data, a spatial basis tensor containing one or more basis images; determine, based on the imaging data, one or more temporal basis tensors, each temporal basis tensor containing one or more basis functions for a respective one of a plurality of temporal dimensions; determine, based on the imaging data, a core tensor that relates the spatial basis tensor to each of the one or more temporal basis tensors; and generate at least one of the plurality of images by multiplying at least (i) the core tensor, (ii) at least a portion of the spatial basis tensor and (iii) at least a portion of at least one of the plurality of temporal basis tensors.

According to aspects of the present disclosure, a non-transitory machine-readable medium having stored thereon instructions for analyzing a multidimensional image tensor containing a plurality of images of a region of interest of a subject, which when executed by at least one processor, cause the at least one processor to: perform one or more imaging scans on the region of interest of the subject to obtain imaging data; determine, based on the imaging data, a spatial basis tensor containing one or more basis images; determine, based on the imaging data, one or more temporal basis tensors, each temporal basis tensor containing one or more basis functions for a respective one of a plurality of temporal dimensions; determine, based on the imaging data, a core tensor that relates the spatial basis tensor to each of the one or more temporal basis tensors; and generate at least one of the plurality of images by multiplying at least (i) the core tensor, (ii) at least a portion of the spatial basis tensor and (iii) at least a portion of at least one of the plurality of temporal basis tensors.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

Figure 1:
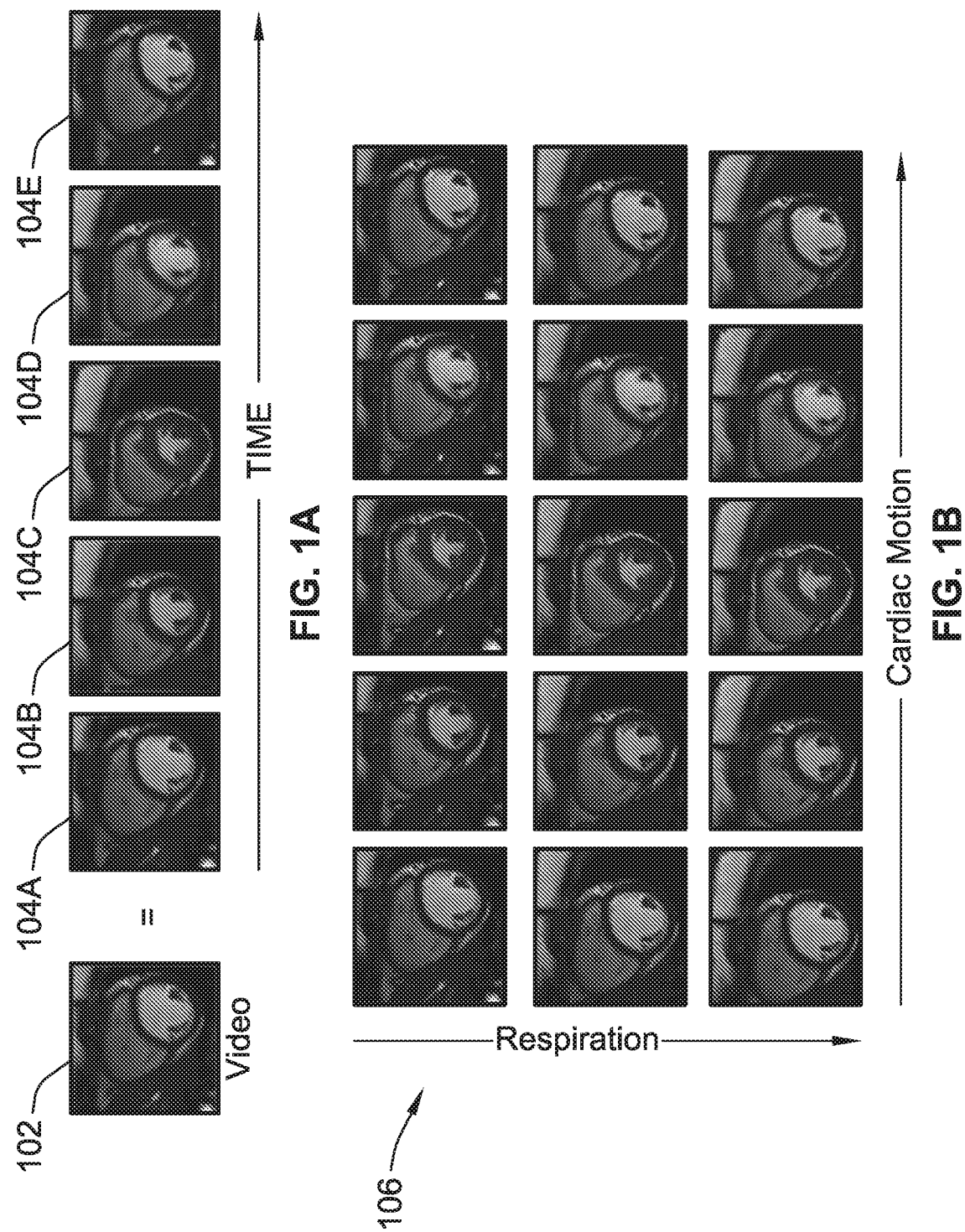
FIG. 1A shows a series of images across time comprising a video, according to aspects of the present disclosure.
FIG. 1B shows an array of images sorted along temporal dimensions, according to aspects of the present disclosure.

While the present disclosure is susceptible to various modifications and alternative forms, specific implementations and embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

While the present disclosure has been described with reference to one or more particular embodiments or implementations, those skilled in the art will recognize that many changes may be made thereto without departing from the spirit and scope of the present disclosure. Each of these embodiments or implementations and obvious variations thereof is contemplated as falling within the spirit and scope of the present disclosure. It is also contemplated that additional embodiments implementations according to aspects of the present disclosure may combine any number of features from any of the embodiments described herein.

Magnetic resonance-based imaging (MR imaging) is a technique most often used for imaging the human body that takes into account principles of nuclear magnetic resonance. For example, doctors and other medical professionals often use MR imaging to view tissue within the human body. Nuclear magnetic resonance is a phenomenon in which nuclei (such as protons in body tissue) localized in a magnetic field emit energy that can be detected. This energy that is detected can be used to create an image. MR imaging generally involves two principle steps. First, the magnetic moment of the nuclei (caused by the intrinsic spin property of elementary particles) are aligned (or polarized) by the presence of an external magnetic field. While in the presence of this external magnetic field, the magnetic moment of each nuclei will generally precess about an axis parallel to the magnetic field. The rate of this precession $\omega$ is generally proportional to $\gamma B_0$, where $B_0$ is the magnitude of the external magnetic field, and $\gamma$ is the gyromagnetic ratio of the nuclei, which is the ratio the nuclei's magnetic moment to its angular momentum. The rate of the precession $\omega$ is considered the nuclei's resonant frequency.

The second principle step in MR imaging is to apply an electromagnetic pulse sequence (usually a radiofrequency, or RF, pulse) to the nuclei. When the frequency of the RF pulses sequence is generally equal to the resonant frequency of the nuclei, the nuclei absorb the energy of the RF pulse and the magnetic moments are rotated out of alignment with the magnetic field. The magnetic moments of the excited nuclei eventually re-align within the presence of the external magnetic field in a process known as relaxation, which has two components. $T_1$ relaxation describes how the component of the magnetic moment parallel to the external magnetic field returns to its initial value. $T_2$ relaxation describes how the components of the magnetic moment perpendicular to the external magnetic field return to their initial value. Because the magnetic moments of nuclei in the external magnetic field without the RF pulse sequence applied are generally parallel to the external magnetic field, $T_1$ relaxation generally describes how parallel component of the magnetic moment returns to its maximum value, while $T_2$ relaxation generally describes how the perpendicular components of the magnetic moment decay. The nuclei of different material relax at different rates and thus emit differing signals, which can be detected and used to form an image identifying the different materials.

Quantitative MR imaging is an application of NMR principles that aims to quantify some characteristic of the tissue being imaged. For example, practitioners may wish to quantify $T_1$ values to detect anomalies such as scar tissue, $T_2$ values to detect tumors, the speed of a contrast agent advancing through tissue to detect ischemia, or diffusion-based characteristics to detect abnormal fiber structure. Various techniques exist to obtain images of a region of interest of a subject/patient that take into account all of these various parameters To obtain images, imaging data of the subject/patient is collected using an MRI equipment. In an example, the region of interest could be the subject's abdomen or chest. In other examples, the region of interest of the subject is more specific, such as the subject's liver, lungs, or heart. The imaging data is dependent on or related to one or more spatially-varying parameters of the region of interest of the subject, such as a voxel location, a contrast agent kinetic parameter, or a diffusion parameter, and is generally indicative of the value or magnitude of the spatially-varying parameters. In some implementations, the spatially-varying parameters can also be time-varying. In other implementations, the spatially-varying parameters can additionally or alternatively be related to physical motion of the region of interest of the subject. Other types of biomedical imaging can also be used to obtain multidimensional images, such as CT scans or CAT scans.

FIG. 1A illustrates a video 102 of a subject's heart from an MM is formed from a series of images 104A-104E. The series of images 104A-104E represent both cardiac motion and respiration over a time period. This series of images 104A-104E thus shows two different time-varying parameters: the phase of the subject's heart within a cardiac cycle, a position of the subject's lungs within a respiratory cycle. FIG. 1B shows an image tensor 106 (which in this example is a matrix) that includes a plurality of images from an MRI that have been separated into multiple temporal dimensions. The x-axis represents different phases of the heart during the cardiac cycle, while the y-axis represents different positions of the lungs during the respiratory cycle. Thus, every image in a given column has the same value for the temporal dimension representing cardiac motion, while every image in a given row has the same value for the temporal dimension representing respiration.

Figure 2:
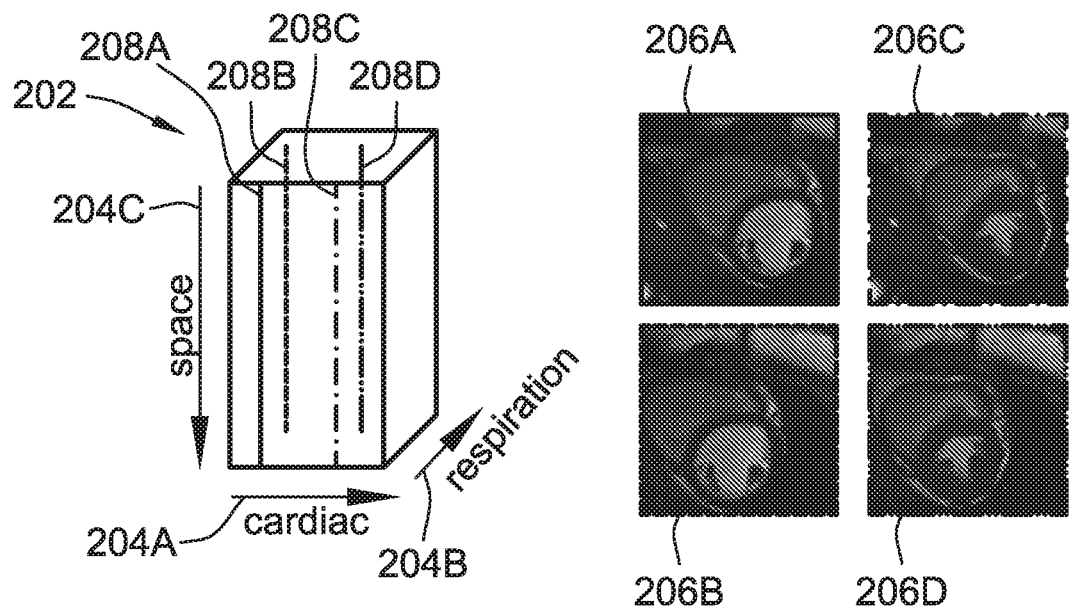
FIG. 2 shows an image tensor containing a plurality of images of a region of interest, according to aspects of the present disclosure.

FIG. 2 shows a representation of an image tensor 202 that contains images representing cardiac motion (a time-varying parameter) along axis 204A and respiratory motion (another time-varying parameter) along axis 204B. Axes 204A and 204B thus represent temporal dimensions. The spatial dimension is represented along axis 204C. Each individual image of the region of interest of the subject can be two-dimensional or three-dimensional. However, each two or three-dimensional image can be reshaped as a vector, which groups all spatial dimensions together. The vector is then placed into a two-dimensional array (comprising cardiac motion on one axis and respiratory motion on the other axis) at the proper time point. The spatial property of the images in a single column do not necessarily vary along a single spatial direction as FIG. 2 may indicate. Rather, each column in the image tensor 202 represents the entire two or three-dimensional image of the region of interest for a given time point, e.g. for a given combination of cardiac motion and respiratory motion values. FIG. 2 also shows four images that are contained in the image tensor 202. Image 206A corresponds to the image represented by vector 208A. Image 206B corresponds to the image represented by vector 208B. Image 206C corresponds to the image represented by vector 208C. Image 206D corresponds to the image represented by vector 208D.

This method of sorting images from a multidimensional MRI can be expanded to any number of different dimensions representing different time-varying parameters. The time-varying parameters can include, but is not limited to: the phase of the subject's heart within a cardiac cycle; the position of the subject's lungs, chest wall, or other organs within a respiratory cycle; a position of a dome of a liver during respiration; a $T_1$ relaxation parameter; an inversion time (or other time since magnetization preparation); a $T_2$ prep duration (or a duration of any magnetization preparation pulse); a diffusion weighting strength; a diffusion weighting direction; an echo time; a dynamic contrast enhancement phase; a flip angle; an elapsed time since the start of scanning; a phase offset of elastographic excitation waves; a frequency offset and duration of saturation preparation pulses (e.g., for chemical exchange saturation transfer); a duration of magnetization transfer preparation pulses; a spectral position (e.g., for spectroscopy); a flow encoding strength; or a flow encoding direction. Thus, all of the images from the MRI can be stored in an image tensor with one or more spatially-varying dimensions and one or more time-varying dimensions. Any given image in the image tensor can show the value of the spatially-varying parameter across the region of interest that was imaged, and can indicate the time period in which the imaging data was collected and the value of the one or more time-varying parameters at that time period.

As noted in the examples, the images are arranged according to common attributes. In another example, the constructed image tensor may have three dimensions. If this image tensor is visualized, the first dimension can be along the x-axis and correspond to the spatial location of a voxels of the images (spatially-varying), the second dimension can be along the y-axis and correspond to the $T_1$ relaxation parameter (time-varying), and the third dimension can be along the z-axis and correspond to a position of the chest wall or liver dome during respiration (time-varying). In this example, the voxels along the x-axis for a given position along the y-axis and the z-axis will all have the same value along the y-axis and the z-axis, e.g. the $T_1$ relaxation parameter and the position of the chest wall or liver dome is the same for each voxel. The same holds true for voxels spaced along the other two dimensions.

Generally, the image tensor is of low-rank rather than full-rank. Full-rank tensors are tensors that produce a full-rank matrix when unfolded or flattened along each of its dimensions. A full-rank matrix is a matrix whose rows or columns (whichever is fewer in amount) are linearly independent. Low-rank tensors are tensors that produce a low-rank matrix when unfolded or flattened along at least one of its dimensions. A low-rank matrix is a matrix whose rows and columns are linearly dependent. With respect to the image tensor, low-rank tensors are generally image tensors where the spatially-varying parameters and the time-varying parameters are able to be accurately described with fewer data points than tensor elements. Images in a low-rank tensor are generally always linearly independent, which is not necessarily true for a full-rank tensor. Low-rank tensors thus can be decomposed into smaller factors without information loss as compared to a full-rank tensor.

Image tensors are useful for isolating a time-varying property of interest and ignoring other properties. By only viewing images where the time-varying property of interest changes and the other time-varying properties are held constant, a doctor or other healthcare professional can more easily analyze the images. Thus, the cardiac motion of a patient can be analyzed at a constant stage in the respiratory cycle so that the movement of the lungs does not affect the images of the patient's heart. However, image tensors can easily become too unwieldy. The number of images in a given image tensor generally grows exponentially with the number of temporal dimensions, which increases the space needed to store the image tensor and the computational time needed to analyze the image tensor.

For example, image tensor 106 of FIG. 1B includes only five cardiac phases and three respiratory phases, and thus only includes fifteen images. However, the number of cardiac and respiratory phases is generally higher, and more temporal dimensions are often involved. Thus, a typical image tensor may include images representing 20 cardiac phases, 6 respiratory phases, 200 inversion times, and 5 $T_2$ prep durations, which results in 120,000 images. This image tensor can easily require over 100 GB of storage space. Moreover, any image analysis operations on the entire image set would generally take at least 120,000 times longer to perform than for a single image.

Figure 3:
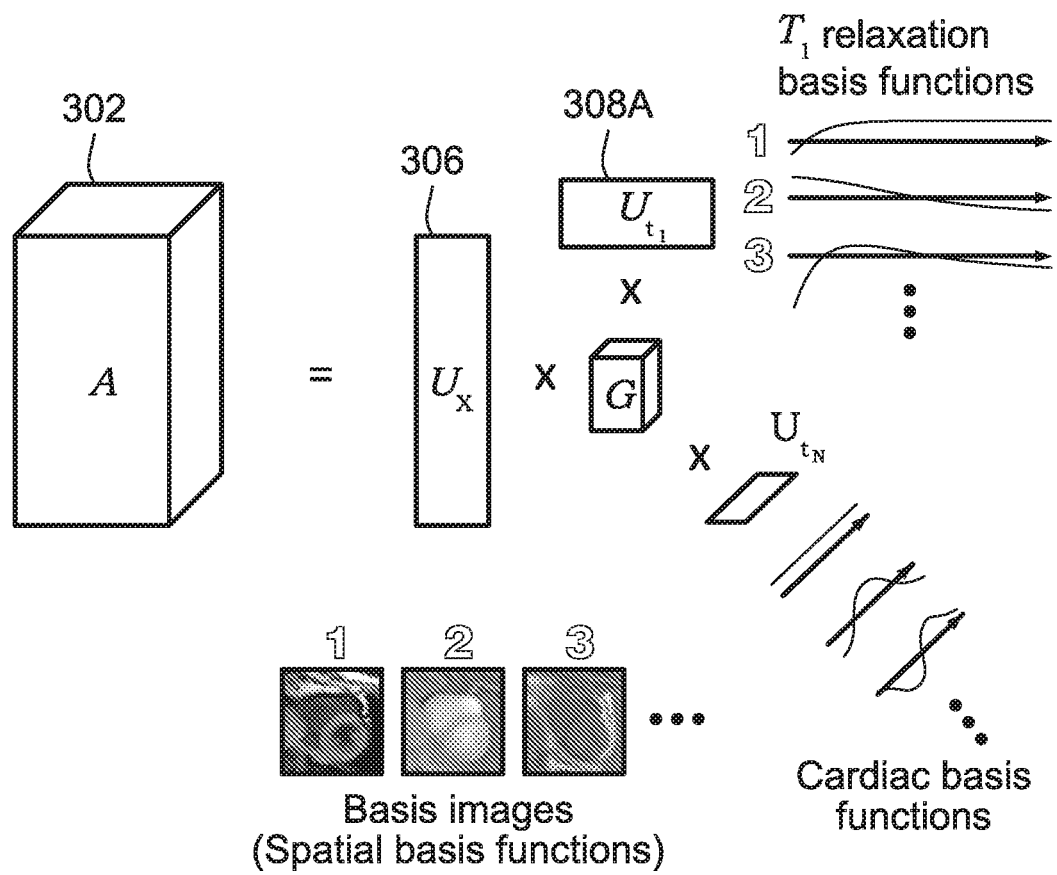
FIG. 3 shows a decomposition of an image tensor containing a plurality of images of a region of interest into a spatial basis tensor, one or more temporal basis tensors, and a core tensor, according to aspects of the present disclosure.

Referring now to FIG. 3, an image tensor 302, which can be the same or similar to image tensor 202, can generally be decomposed into a number of tensor factors. Because the images in image tensor 302 are correlated with each other, they can generally be modeled as being linearly dependent. This causes image tensor 302 to be low-rank, which means that the image tensor 302 can be decomposed or factorized. Any number of low-rank tensor decompositions can be used. In some implementations, a Tucker decomposition is used.

The Tucker decomposition reduces the image tensor 302 into the product of a core tensor 304, a spatial basis tensor 306, and a number of temporal basis tensors 308A and 308B. In some implementations, the spatial basis tensor 306 and the temporal basis tensors 308A and 308B can be matrices, e.g., two-dimensional arrays. However, any of the tensors discussed herein can generally have any number of dimensions, depending on the number of time-varying parameters that are being measured. The image tensor 302 can thus be represented by the following equation:

$$\mathcal{A} = \mathcal{G} \times_1 U_x \times_2 U_{t_1} \times_3 U_{t_2} \times_4 \ldots \times_{(N+1)} U_{t_N}$$

In this equation, the $\times_i$ operator denotes the ith mode product, $U_x$ denotes the spatial basis tensor 306, $U_{t_i}$ denotes the temporal basis tensors 308A, 308B, or other temporal basis tensors, and $\mathcal{G}$ denotes the core tensor 304. The spatial basis tensor 306 contains one or more basis images (which are generally considered to be spatial basis functions), while each temporal basis tensor 308A, 308B contains one or more basis functions for the temporal dimensions (e.g. for each time-varying parameter of the subject). The core tensor 304 relates the spatial basis tensor 306 to each of the temporal basis tensors 308A and 308B. Depending on the complexity of the time-varying parameters of the subject, the number of basis functions needed to accurately describe all of the images can vary. For example, images from a patient with simple cardiac motion will likely require fewer basis functions for the temporal basis tensor related to cardiac motion than for a patient with a complex cardiac motion.

Generally, the decomposed basis tensors have far fewer elements than the total number of elements in the image tensor itself. The number of elements generally grows linearly with the number of temporal dimensions, rather than exponentially. Thus, the basis tensors and the core tensor require less storage space to store and less computational time to analyze.

In some implementations, when a low-rank tensor model is used for image reconstruction, the basis tensors are already known, and may have never even been multiplied to form the image tensor. In this case, the compression from the tensor decomposition has generally already been performed and may be lossless. In other implementations, only the whole image tensor is known, in which case a tensor decomposition algorithm such as high-order singular value decomposition (HOSVD) can be applied and truncated to produce small tensor factors. IN this case, compression may be lossy.

In one example of the storage saving gained by the decomposition, the image tensor can be stored as a 20×6×5×5 core tensor, a spatial basis tensor containing 50 basis images, a first temporal basis tensor containing 20 basis functions related to the cardiac phase, a second temporal basis tensor containing 6 basis functions related to the respiratory phase, a third temporal basis tensor containing 5 basis functions related to the inversion time, and a fourth temporal basis tensor containing 5 basis functions related to the $T_2$ prep duration. If the temporal dimensions generally have the same number of values discussed in the earlier example, the first temporal basis tensor includes 20 basis functions×20 cardiac positions=400 elements; the temporal basis tensor includes 6 basis functions×6 respiratory positions=36 elements; the third temporal basis tensor includes 5 basis functions×200 inversion times=500 elements; and the fourth temporal basis tensor includes 5 basis functions×5 $T_2$ prep durations=25 elements. In this example, the basis tensors and the core tensors can have storage requirements of only about 200 MB. Moreover, the individual basis tensors can also be compressed using other established compression algorithms such as JPEG, ZIP, or any other suitable compression algorithm.

In some implementations, the image tensor 302 is only partially decomposed, or is fully decomposed and then two or more of the core tensor and the basis tensors are pre-multiplied. For example, it may be more storage-efficient to pre-multiply the core tensor and some of the temporal basis tensors. It may also be preferable to pre-multiply the core tensor and all of the temporal basis tensors to save computational time during analysis, even if this does not save as much storage space. Generally, any combination of the core tensor, the spatial basis tensor, and the temporal basis tensors can be pre-multiplied to minimize storage requirements, minimize required computational time during analysis, or some combination of both.

Figure 4A:
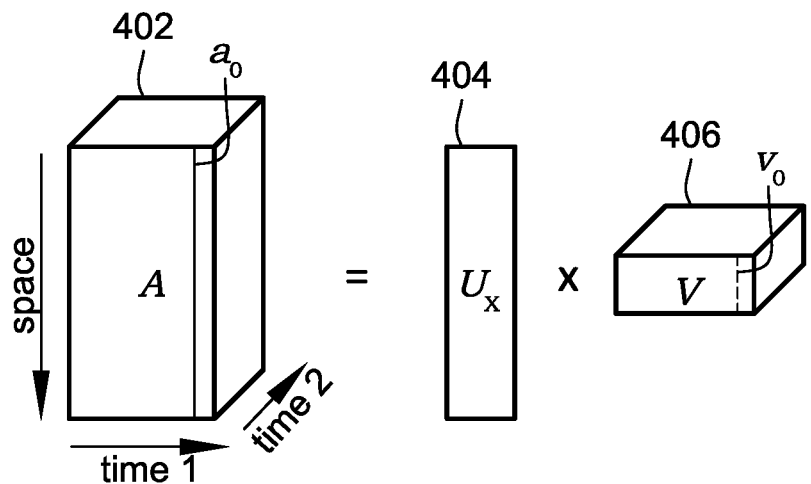
FIG. 4A shows a process for generating one image from the image tensor of FIG. 3, according to aspects of the present disclosure.
Figure 4B:
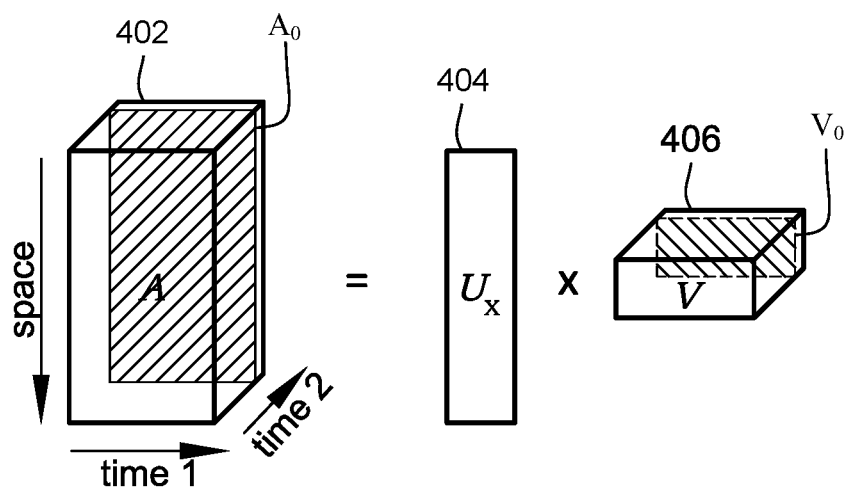
FIG. 4B shows a process for generating multiple images from the image tensor of FIG. 3, according to aspects of the present disclosure.
Figure 4C:
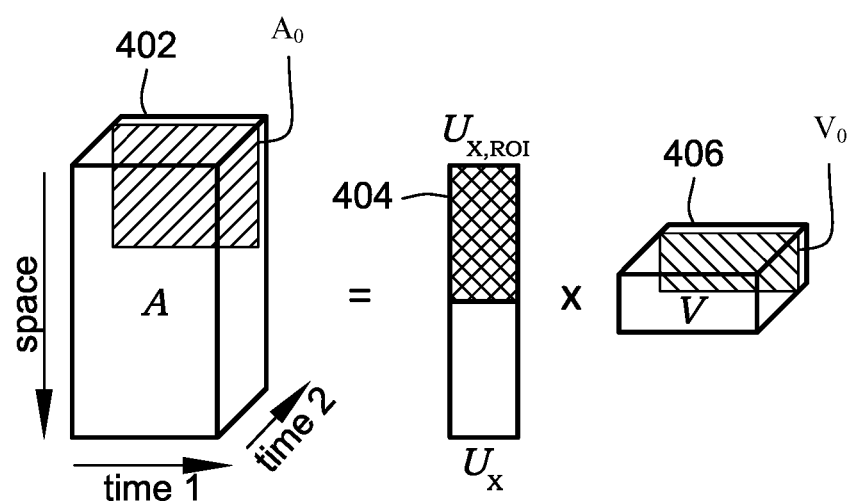
FIG. 4C shows a process for generating multiple images showing a region smaller than the region of interest from the image tensor of FIG. 3, according to aspects of the present disclosure.

Referring now to FIGS. 4A-4C, selective multiplication of the core tensor, the spatial basis tensor, and the one or more temporal basis tensors can be used to generate any of the images of the region of interest that are part of the full image tensor. FIG. 4A illustrates a process for generating a desired image that is stored in the image tensor 402. This desired image is represented by vector $a_o$, which is a vector of the spatial dimension (e.g., an image of the region of interest) at a desired time point. The image tensor 402 shows only two temporal dimensions, although the image tensor 402 can account for any suitable number of temporal dimensions. The desired image is generated by multiplying the spatial basis tensor 404 by a single vector $v_0$ of modified temporal basis tensor 406. Modified temporal basis tensor 406 is determined by multiplying the core tensor and some or all of the temporal basis tensors. In other implementations, some or all of this multiplication can be pre-multiplication, e.g. is performed as the images are initially generated during the MRI process, rather than later when the image is needed. In other implementations, some or all of the multiplication to obtain the modified temporal basis tensor 406 is performed in real-time. The vector of the modified temporal basis tensor 406 that is used is representative of the desired time point of the image vector $a_0$. The result of this multiplication is a single image of the region of interest at a desired time point.

FIG. 4B illustrates the process for generating multiple images of the region of interest that allow at least one of the temporal dimensions to vary. FIG. 4B generally shows a similar process as FIG. 4A. However, the multiple images are represented by a matrix $A_0$, rather than a single vector $a_0$. As shown, the multiple images in the image tensor 402 represented by matrix $A_0$ all have the same value along one of the temporal dimensions ("time 2"), but have different values along the other temporal dimension ("time 1"). The spatial basis tensor 404 is multiplied by a slice $V_0$ of the modified temporal basis tensor 406. Slice $V_0$ is taken from the modified temporal basis tensor 406 at the same points in time as the points in time represented by the images in matrix $A_0$ of the image tensor 402. Generally, any given subset of the modified temporal basis tensor 406 can be used to generate the multiple images. In an example, the set of images could show the varying phase of the subject's heart within the cardiac cycle while any motion due to respiration is held constant, e.g. while the chest cavity is in the same position.

FIG. 4C illustrates the process for generating multiple images of a region smaller than the region of interest. The process of FIG. 4C is similar to the process of FIG. 4B, except that only a subset of the spatial basis tensor 404 that corresponds to the desired region is used. While not shown, a subset of the spatial basis tensor 404 can be multiplied by a single vector of the modified temporal basis tensor 406 (as in FIG. 4A) to generate a single image of the region smaller than the region of interest. Thus, generally any single image or set of images can be generated from the core tensor, the spatial basis tensor, and the temporal basis tensors by multiplying the core tensors and the appropriate portions of the spatial basis tensor and the temporal basis tensors.

This selective multiplication can be used on-demand to generate images when requested by a user. In one example, a user interface includes a slider for each of the temporal dimensions. The user can move the sliders to generate and view images for any combination of values of the temporal dimensions. In some implementations, each image is generated only when requested by the user. In other implementations, multiple images along a single temporal dimension can be generated based on the user's first interaction with the corresponding slider to produce a single image, based on the assumption that the user will want to continue viewing images along that temporal dimension.

Other processes can be used to analyze the spatial basis tensor and the temporal basis tensors. These processes can directly analyze or process the basis tensor in lieu of analyzing or processing the full set of images directly. In one example, multiplanar reconstruction, which is the reformatting of image volumes along arbitrarily-oriented slices, can be used. Generally, this reformatting would be done for every image in the image tensor, or for every image chosen for display. However, because this is purely spatial processing, the basis images in the spatial basis tensor can be directly reformatted prior to selective multiplication. Because there are many fewer images in the spatial basis tensor, this is much faster than performing multiplanar reconstruction on individual images.

In some implementations, the basis images in the spatial basis tensor are pre-processed to modify a spatial characteristic, such as the spatial orientation of the basis images. This can reformat the images along arbitrarily-oriented slices. Other types of spatial characteristics can also be modified. In other implementations, temporal processing can be done directly on the temporal basis functions of the temporal basis tensors to modify a temporal characteristic of the temporal basis functions. In still other implementations, machine-learning based analysis can be used directly on the basis tensors without having to fully multiply the tensors.

Figure 5:
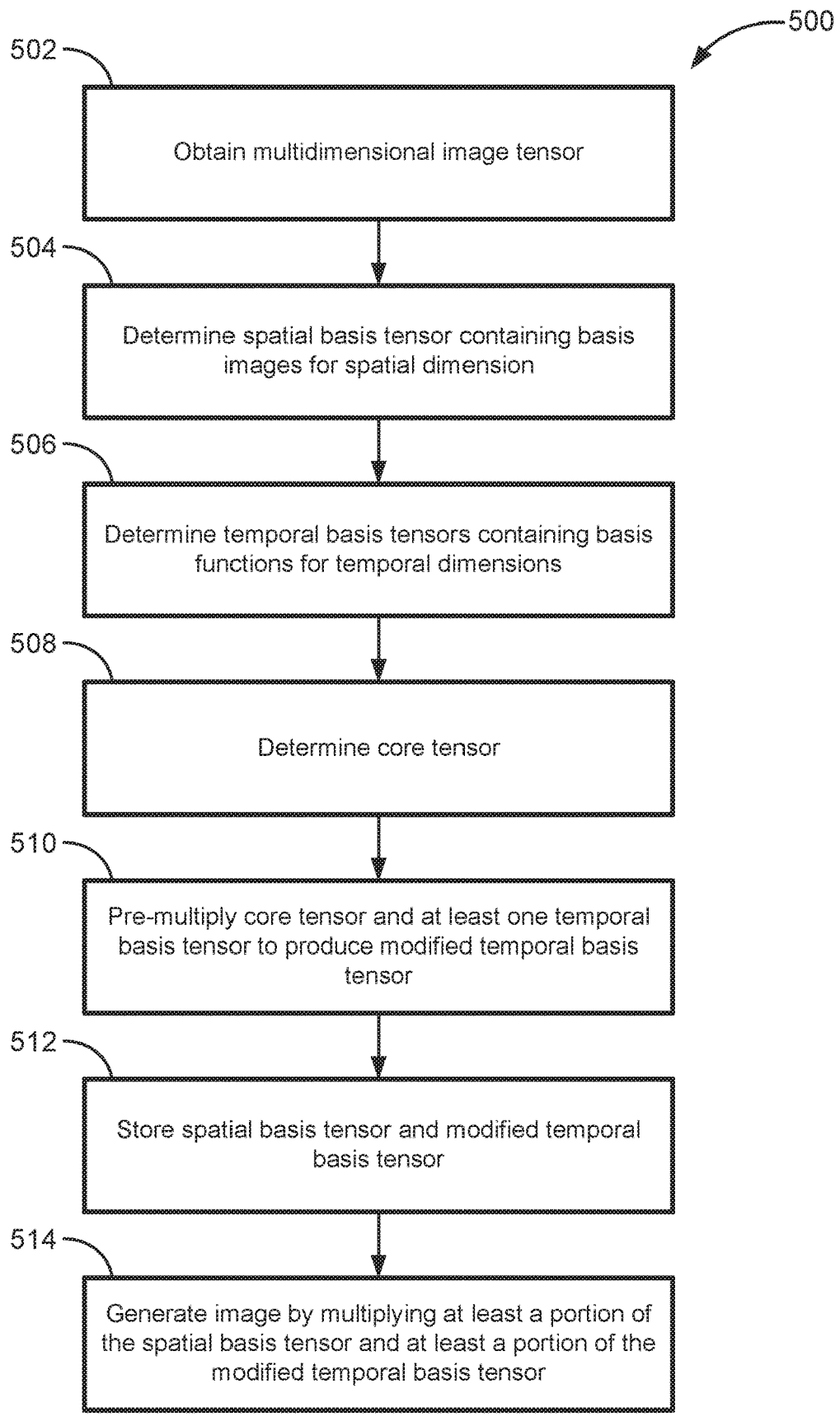
FIG. 5 shows the steps of a method for analyzing a multidimensional image tensor containing a plurality of images, according to aspects of the present disclosure.

Referring now to FIG. 5, a method 500 for analyzing a multidimensional image tensor containing a plurality of images of a region of interest of a subject is shown. At step 502, one or more imaging scans are performed to obtain the multidimensional image tensor. The imaging scans produce imaging data, which is used to generate the multidimensional image tensor. The imaging scans are generally MRI scans, although other scans such as CT scans and CAT scans can also be used. To collect the imaging data, an RF pulse sequence is applied to the region of interest of the subject. The resulting signal(s) are then measured. Thus, the RF pulse sequence may be designed using saturation recovery pulses to measure $T_1$ relaxation, $T_2$ prep pulses to measure $T_2$ relaxation, or any other specific pulse sequence to measure a specific spatially-varying parameter or combination of spatially-varying parameters. There is generally a pause after each RF pulse of the RF pulse sequence to allow for the resulting signal to be measured. In some implementations, the imaging data is collected in a semi-continuous mode. In the semi-continuous mode, the RF pulse sequence contains additional pauses to allow the $T_1$ signal to recover (as measurement can reduce/saturate the $T_1$ signal). In other implementations, the imaging data is collected in a continuous mode, where the applied RF pulse sequence is not paused to allow the $T_1$ signal to recover, and only contains pauses to allow for measurement of the resulting signal. In either implementation, the applied RF pulse sequence is not paused to wait for any particular respiratory position, but rather the subject is allowed to breathe freely.

At step 504, as part of the decomposition process, the spatial basis tensor is determined. The spatial basis tensor contains one or more basis images representative of a spatial dimension. The spatial basis tensor represents all possible values of the spatial dimension in the images. At step 506, one or more temporal basis tensors are determined. Each temporal basis tensor contains one or more basis functions for a respective temporal dimension. Thus, one temporal basis tensor may contain one or more basis functions related to cardiac motion, while another temporal basis tensor contains one or more basis functions related to respiratory motion. The temporal basis tensors represent all possible values of each of the temporal dimensions in the images. The temporal dimensions can include the phase of the subject's heart within the cardiac cycle, the position of the subject's lungs within the respiratory cycle, the inversion time of the MRI imaging sequence, and the $T_2$ prep duration of the MRI imaging sequence.

At step 508, the core tensor is determined. The core tensor relates the spatial basis tensor to each of the one or more temporal basis tensors. At step 510, the core tensor and at least one of the temporal basis tensors are pre-multiplied to produce a modified temporal basis tensor. The pre-multiplying of the core tensor and the at least one of the one or more temporal basis tensors is generally configured to minimize or reduce (i) the computation time required to generate the at least one of the plurality of images, (ii) the amount of storage need to store the core tensor and the at least one of the one or more temporal basis tensors, or (iii) both (i) and (ii). In some implementations, the modified temporal basis tensor is produced by pre-multiplying the core tensor and all of the temporal basis tensors. In other implementations, the modified temporal basis tensor is produced by pre-multiplying the core tensor and only some of the temporal basis tensors.

At step 512, the spatial basis tensor and the modified temporal basis tensor are stored. At step 514, at least one image of the plurality of images from the image tensor is generated by multiplying, at least a portion of the spatial basis tensor, at least a portion of the modified temporal basis tensor, and any other necessary tensors. In some implementations, the modified temporal basis tensor is produced by pre-multiplying the core tensor and all of the temporal basis tensors. In this implementation, the image(s) is generated by multiplying only at least a portion of the spatial basis tensor and at least a portion of the modified temporal basis tensor. In other implementations, the temporal basis tensors include a first set and a second set, and the modified temporal basis tensor is produced by pre-multiplying the core tensor and only the first set of the temporal basis tensors. In this implementation, the image(s) is generated by multiplying at least a portion of the spatial basis tensor, at least a portion of the modified temporal basis tensor, and at least a portion of the second set of temporal basis tensors.

To generate a single image, the spatial basis tensor and a vector of the modified temporal basis tensor are multiplied. If the temporal basis tensor is created by pre-multiplying less than all of the temporal basis tensors, a corresponding vector of each of the remaining temporal basis tensors are also included in this selective multiplication. This vector represents the value of the temporal dimensions at the point in time of the desired image. To generate multiple images, the spatial basis tensor and a subset of the modified temporal basis tensors (and a corresponding subset of any remaining temporal basis tensors) are multiplied. The subset of the modified temporal basis tensor and any remaining temporal basis tensor represents the value of the temporal dimensions for every time point that the multiple images cover. In either of these implementations, an image or images of less than the entire region of interest of the subject that was imaged (and thus data was collected for) can be generated by multiplying only a subset of the spatial basis tensor.

In some implementations, the multidimensional image tensor is not generated or derived from the imaging data. Instead, the spatial basis tensor, the temporal basis tensors, and the core tensor are generated or derived directly from the imaging data. In other implementations, there is no pre-multiplying of any of the basis tensors, and instead the image(s) are generated by multiplying the core tensor, at least a portion of the spatial basis tensor, and at least a portion of one or more of the temporal basis tensors.

Figure 6:
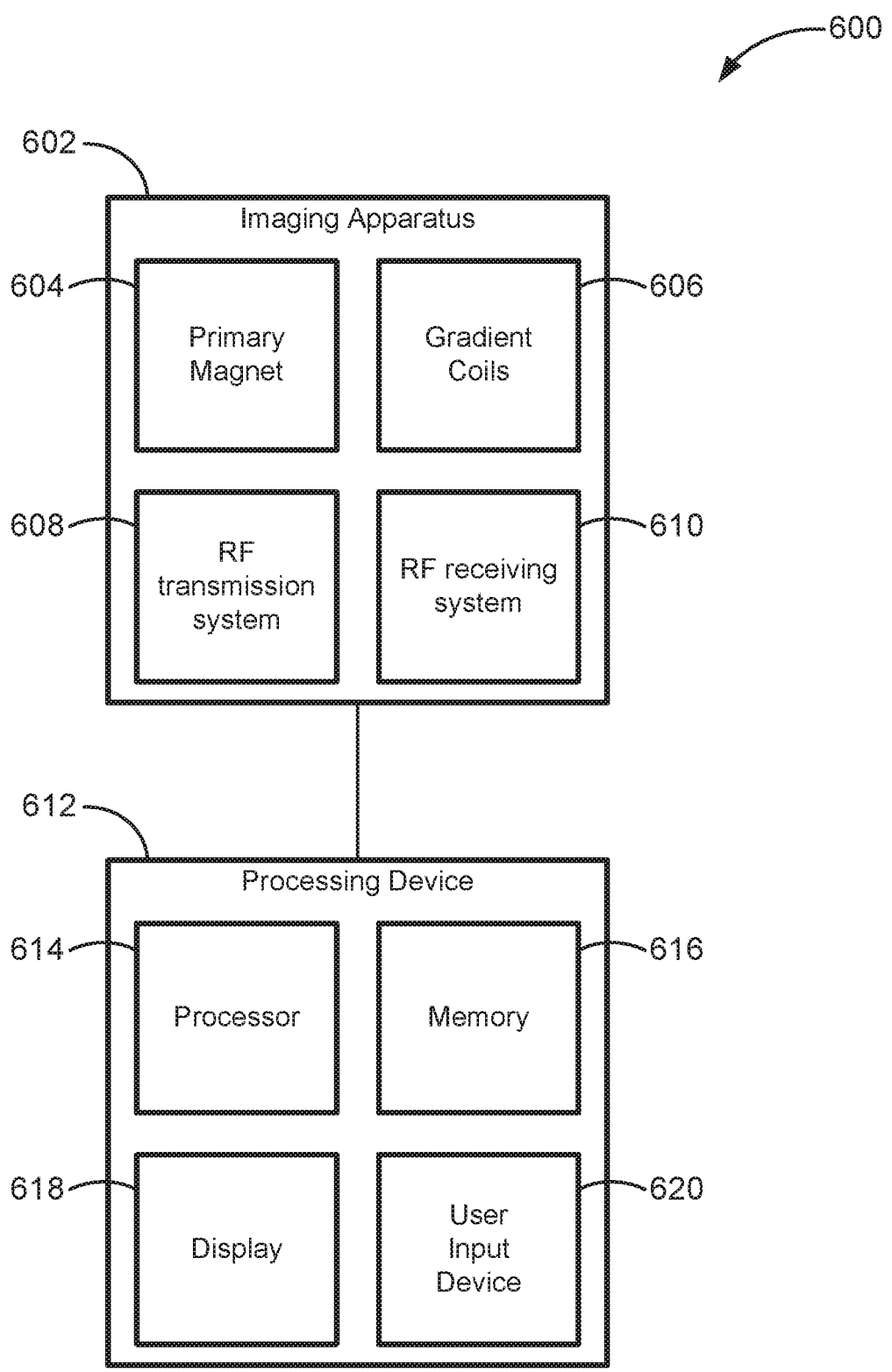
FIG. 6 shows a system for analyzing a multidimensional image tensor containing a plurality of images, according to aspects of the present disclosure.

Aspects of the present disclosure can be implemented using a variety of hardware. One such implementation is illustrated in FIG. 6. A system 600 for performing magnetic resonance imaging on a subject includes an imaging apparatus 602 and a processing device 612. The imaging apparatus 602 can be one used for standard magnetic resonance imaging, and can include a primary magnet 604, gradient coils 606, an RF transmission system 608, and an RF receiving system 610. The primary magnet 604 can be a permanent magnet, an electromagnet (such as a coil), or any other suitable magnet. Primary magnet 604 is used to create the external magnet field that is applied to the sample during imaging. Gradient coils 606 create a secondary magnet field that distorts the external magnetic field and can cause the resonant frequency of the protons in the sample to vary by position. The gradient coils 606 can thus be used to spatially encode the positions of protons throughout the sample, e.g. can be used to select which plane intersecting the sample will be used for imaging. The RF transmission system 608 is used to apply the RF pulse sequence that provides energy to the protons in the sample to rotate their magnet moments out of alignment with the external magnetic field, and saturates the solute material protons. The RF transmission system 608 generally includes a frequency generator (such as an RF synthesizer), a power amplifier, and a transmitting coil. The RF receiving system 610 receives the signals emitted by the protons in the sample as they relax back to their standard alignment. The RF receiving system 610 can a receiving coil to receive the emitted signals, and a pre-amplifier for boosting the received signals and ensuring the signals are suitable for processing. In some implementations, the RF receiving system 610 can include a signal processing component that processes the received signals to provide data that is usable by the processing device 612. Each of the component of the imaging apparatus can be disposed within one or more housings.

The processing device 612 can be communicatively coupled to the imaging apparatus 602, and can include a processor 614, processor-executable memory 616, a display 618, and a user input device 620. The processing device 612 is used to manage the operations of the imaging apparatus 602, and can thus be configured to cause the imaging apparatus 602 to perform multidimensional imaging according to the principles disclosed herein. System 600 can also include one or more additional processing devices such that various tasks required to perform multidimensional imaging can be performed by different processing devices. For example, system 600 may include other processing devices or systems that analyze the imaging data and reconstruct the images from the imaging data. System 600 can also include one or more printers, one or more network interfaces, or one or more other types of hardware.

In some implementations, a non-transitory, machine-readable medium has instructions stored thereon for implementing any of any of the methods or processes discussed herein. A machine processor is configured to executed the instructions in order to perform these methods or processes.

Aspects of the present disclosure can be implemented on a variety of types of processing devices, such as general purpose computer systems, microprocessors, digital signal processors, micro-controllers, application specific integrated circuits (ASICs), programmable logic devices (PLDs) field programmable logic devices (FPLDs), programmable gate arrays (PGAs), field programmable gate arrays (FPGAs), mobile devices such as mobile telephones, personal digital assistants (PDAs), or tablet computers, local servers, remote servers, wearable computers, or the like.

Memory storage devices of the one or more processing devices can include a machine-readable medium on which is stored one or more sets of instructions (e.g., software) embodying any one or more of the methodologies or functions described herein. The instructions can further be transmitted or received over a network via a network transmitter receiver. While the machine-readable medium can be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media. A variety of different types of memory storage devices, such as a random access memory (RAM) or a read only memory (ROM) in the system or a floppy disk, hard disk, CD ROM, DVD ROM, flash, or other computer readable medium that is read from and/or written to by a magnetic, optical, or other reading and/or writing system that is coupled to the processing device, can be used for the memory or memories.

While aspects of the present disclosure have been described with reference to one or more particular implementations, those skilled in the art will recognize that many changes may be made thereto without departing from the spirit and scope of the present disclosure. Each of these implementations and obvious variations thereof are contemplated as falling within the spirit and scope of the present disclosure. It is also contemplated that additional implementations according to aspects of the present disclosure may combine any number of features from any of the implementations described herein.

REFERENCES

The following documents are provided to explain various aspects of the present invention. Their contents of each is hereby incorporated by reference herein in its entirety.
1. Christodoulou, A. G. et al. Magnetic resonance multitasking for motion-resolved quantitative cardiovascular imaging. *Nature Biomed Eng* 2, 215-226, doi:10.1038/s41551-018-0217-y (2018).
2. Feng, L. et al. XD-GRASP: Golden-angle radial MRI with reconstruction of extra motion-state dimensions using compressed sensing. *Magn Reson Med* 75, 775-788 (2016).
3. Cheng, J. Y. et al. Comprehensive multi-dimensional MRI for the simultaneous assessment of cardiopulmonary anatomy and physiology. *Sci Rep* 7, 5330 (2017).
4. Liang, Z.-P. in *Proc IEEE Int Symp Biomed Imaging* 988-991 (2007)
5. Tucker, L. R. Some mathematical notes on three-mode factor analysis. *Psychometrika* 31, 279-311 (1966).
6. De Lathauwer, L., De Moor, B. & Vandewalle, J. A multilinear singular value decomposition. *SIAM J Matrix Anal Appl* 21, 1253-1278 (2000).

What is claimed is:

1. A method of analyzing image data associated with a region of interest of a subject, the method comprising:
    performing one or more imaging scans on the region of interest of the subject to obtain the imaging data;
    determining, based on the imaging data, a spatial basis tensor containing one or more basis images;
    determining, based on the imaging data, one or more temporal basis tensors, each temporal basis tensor containing one or more basis functions for a respective one of a plurality of temporal dimensions;
    determining, based on the imaging data, a core tensor that relates the spatial basis tensor to each of the one or more temporal basis tensors;
    multiplying the core tensor and the one or more temporal basis tensors to produce a modified temporal basis tensor; and
    generating a plurality of images by multiplying (i) at least a portion of the spatial basis tensor and (ii) only a portion of the modified temporal basis tensor,
    wherein the portion of the modified temporal basis tensor includes the one or more basis functions for a first temporal dimension of the plurality of temporal dimensions and does not include the one or more basis functions for a second temporal dimension of the plurality of temporal dimensions, such that the plurality of images show the region of interest while the first temporal dimension varies over time and the second temporal dimension is held constant.

2. The method of claim 1, wherein the plurality of temporal dimensions includes at least one of a phase of the subject's heart within a cardiac cycle, a position of the subject's lungs within a respiratory cycle, a position of a dome of a liver during respiration, an inversion time, a time since magnetization preparation, a $T_2$ prep duration, a duration of a magnetization preparation pulse, a diffusion weighting strength, a diffusion weighting direction, an echo time, a dynamic contrast enhancement phase, a flip angle, an elapsed time since the start of scanning, a phase offset of elastographic excitation waves, a frequency offset of saturation preparation pulses, a duration of saturation preparation pulses, a duration of magnetization transfer preparation pulses; a spectral position, a flow encoding strength, or a flow encoding direction.

3. The method of claim 1, wherein the generating of the plurality of images includes multiplying all of the spatial basis tensor by the portion of the modified temporal basis tensor such that the plurality of images show all of the region of interest.

4. The method of claim 1, wherein the generating of the plurality of images includes multiplying only a portion of the spatial basis tensor by the portion of the modified temporal basis tensor such that the plurality of images show only a portion of the region of interest.

5. The method of claim 1, further comprising pre-processing at least one of the spatial basis tensor and the one or more temporal basis tensors.

6. The method of claim 5, wherein the pre-processing of at least one of the spatial basis tensor and the one or more temporal basis tensors includes performing multiplanar reconstruction.

7. The method of claim 5, wherein the one or more basis images of the spatial basis tensor are pre-processed to modify a spatial characteristic of the one or more basis images.

8. The method of claim 7, wherein the spatial characteristic is a spatial orientation.

9. The method of claim 5, wherein the one or more basis functions of at least one of the one or more temporal basis tensors are pre-processed to modify a temporal characteristic of the one or more basis functions of the one or more temporal basis tensors.

10. The method of claim 1, further comprising storing the spatial basis tensor and the modified temporal basis tensor prior to generating the plurality of images.

11. The method of claim 1, wherein multiplying the core tensor and the one or more temporal basis tensors minimizes (i) a computation time required to generate the plurality of images, (ii) an amount of storage needed to store the core tensor and the one or more temporal basis tensors, or (iii) both (i) and (ii).

12. The method of claim 1, further comprising generating a multidimensional image tensor from the imaging data, such that the spatial basis tensor, the one or more temporal basis tensors, and the core tensor are all determined based on the multidimensional image tensor.

13. A system for analyzing image data associated with a region of interest of a subject, comprising:
a magnet operable to provide a magnetic field;
a transmitter operable to transmit to a region within the magnetic field;
a receiver operable to receive a magnetic resonance signal from the region with the magnetic field; and
a processor operable to control the transmitter and the receiver, the processor being configured to:
perform one or more imaging scans on the region of interest of the subject to obtain imaging data;
determine, based on the imaging data, a spatial basis tensor containing one or more basis images;
determine, based on the imaging data, one or more temporal basis tensors, each temporal basis tensor containing one or more basis functions for a respective one of a plurality of temporal dimensions;
determine, based on the imaging data, a core tensor that relates the spatial basis tensor to each of the one or more temporal basis tensors;
multiplying the core tensor and the one or more temporal basis tensors to produce a modified temporal basis tensor; and
generate a plurality of images by multiplying (i) at least a portion of the spatial basis tensor and (ii) only a portion of the modified temporal basis tensor,
wherein the portion of the modified temporal basis tensor includes the one or more basis functions for a first temporal dimension of the plurality of temporal dimensions and does not include the one or more basis functions for a second temporal dimension of the plurality of temporal dimensions, such that the plurality of images show the region of interest while the first temporal dimension varies over time and the second temporal dimension is held constant.

14. A non-transitory machine-readable medium having stored thereon instructions for analyzing image data associated with a region of interest of a subject, which when executed by at least one processor, cause the at least one processor to:
perform one or more imaging scans on the region of interest of the subject to obtain imaging data;
determine, based on the imaging data, a spatial basis tensor containing one or more basis images;
determine, based on the imaging data, one or more temporal basis tensors, each temporal basis tensor containing one or more basis functions for a respective one of a plurality of temporal dimensions;
determine, based on the imaging data, a core tensor that relates the spatial basis tensor to each of the one or more temporal basis tensors;
multiply the core tensor and the one or more temporal basis tensors to produce a modified temporal basis tensor; and
generate a plurality of images by multiplying (i) at least a portion of the spatial basis tensor and (ii) only a portion of the modified temporal basis tensor,
wherein the portion of the modified temporal basis tensor includes the one or more basis functions for a first temporal dimension of the plurality of temporal dimensions and does not include the one or more basis functions for a second temporal dimension of the plurality of temporal dimensions, such that the plurality of images show the region of interest while the first temporal dimension varies over time and the second temporal dimension is held constant.

* * * * *